United States Patent [19]

Delgado et al.

[11] Patent Number: 5,614,310
[45] Date of Patent: Mar. 25, 1997

[54] LOW TRAUMA WOUND DRESSING WITH IMPROVED MOISTURE VAPOR PERMEABILITY

[75] Inventors: Joaquin Delgado, Stillwater; Richard J. Goetz; Spencer F. Silver, both of Woodbury; Donald H. Lucast, North St. Paul, all of Minn.

[73] Assignee: Minnesota Mining and Manufacturing Company, St. Paul, Minn.

[21] Appl. No.: 334,683

[22] Filed: Nov. 4, 1994

[51] Int. Cl.⁶ ........................................... C09J 7/02
[52] U.S. Cl. ........................ 428/316.6; 428/317.3; 428/317.5; 428/317.9; 428/343; 428/355 AC
[58] Field of Search .................... 428/316.6, 317.3, 428/317.5, 317.9, 343, 355

[56] References Cited

U.S. PATENT DOCUMENTS

| | | | |
|---|---|---|---|
| 3,691,140 | 9/1972 | Silver | 260/78.5 |
| 3,857,731 | 12/1974 | Merrill, Jr. | 117/122 |
| 4,166,152 | 8/1979 | Baker et al. | 428/522 |
| 4,595,001 | 6/1986 | Potter et al. | 128/156 |
| 4,793,003 | 12/1988 | Riedel et al. | 2/15 |
| 4,798,201 | 1/1989 | Rawlings et al. | 128/156 |
| 4,994,322 | 2/1991 | Delgado et al. | 428/343 |
| 5,045,569 | 9/1991 | Delgado | 521/60 |

FOREIGN PATENT DOCUMENTS

| | | |
|---|---|---|
| 0353972 | 1/1986 | European Pat. Off. . |
| WO84/03837 | 10/1984 | WIPO ............ A61L 15/06 |
| WO93/02717 | 2/1993 | WIPO ............ A61L 15/44 |
| WO94/13751 | 6/1994 | WIPO ............ C09J 133/08 |
| WO94/24177 | 10/1994 | WIPO ............ C08F 220/18 |

OTHER PUBLICATIONS

Absorbents/Adsorbents, 1993 Fucntional Materials, North American, pp. 2–11.

Primary Examiner—Jenna Davis
Attorney, Agent, or Firm—Michael S. Sherrill

[57] ABSTRACT

We have discovered a low trauma wound dressing including a moisture-vapor permeable backing and a contiguous particulate adhesive layer comprised of tacky, substantially solvent-insoluble, solvent-dispersible, acrylate-based, elastomeric, pressure-sensitive adhesive microspheres.

44 Claims, No Drawings

LOW TRAUMA WOUND DRESSING WITH IMPROVED MOISTURE VAPOR PERMEABILITY

FIELD OF THE INVENTION

This invention relates to wound dressings. More specifically, this invention relates to wound dressing tapes having a pressure sensitive adhesive layer for securing the dressing ever the wound.

BACKGROUND OF THE INVENTION

Wound dressing tapes intended for application to wounds that exude bodily fluids should prevent the introduction of bacteria or other pathogens into the wound while permitting maximum evaporation of exuded fluids. At the same time, such tapes should also provide good initial adhesion—in order to prevent premature release of the tape—and minimal build-up of adhesion—so as to minimize skin trauma upon removal of the tape.

Commercially available wound dressing tapes typically include either a rubber-based or an acrylic-based adhesive with acrylic-based adhesives generally favored because of their hypoallergenic nature.

While the hypoallergenic nature of an adhesive is one factor to be considered in assessing acceptability of the adhesive for use in a wound dressing tape, traumatization of skin upon removal of a wound dressing tape is primarily correlated to changes in the cohesion of skin cells resulting from prolonged coverage of the skin with an occlusive tape or bandage. The type and severity of skin injury resulting from the removal of many conventional wound dressing tapes varies with the length of time the tape is worn. The longer a tape is worn, the more hydrated and thus macerated the outer layer of the stratum corneum becomes. The internal strength of the stratum corneum can be significantly reduced when macerated in this manner, resulting in deep and irregular fractures within the stratum corneum upon removal of a wound dressing tape. When occlusive medical tape is worn for short intervals of time—such as a few minutes—the upper layer of the stratum corneum will not gain significant fluid from the underlying skin layers and the tape can be removed without significant trauma to the skin. However, when occlusive medical tape is worn on the skin for prolonged periods—such as twenty four hours—fluids will build-up in the upper layers of the stratum corneum and frequently result in severe skin fractures upon removal of the tape.

Trauma to the skin can be lessened when the wound dressing tape permits evaporation of fluids from underneath the tape. This fact has led to the development and sale of wound dressing tapes which provide a high moisture vapor transmission rate.

Potter (U.S. Pat. No. 4,595,001) discloses formation of a moisture vapor transmissive wound dressing tape by pattern coating an adhesive onto a backing so as to leave a significant percentage of the backing in direct contact with the skin.

Rawlings (U.S. Pat. No. 4,798,201) discloses formation of a porous, moisture vapor permeable adhesive film for use in a wound dressing which is formed by coating a mixture of an emulsion adhesive and petroleum spirits onto a silicone release liner or backing film.

Takemote (European Patent Application Publication 0 353 972) discloses formation of a moisture vapor transmissive wound dressing tape by dot coating an adhesive onto a backing so as to leave a significant percentage of the backing available for direct contact with the skin.

Silver (U.S. Pat. No. 3,691,140) discloses formation of a porous, moisture vapor permeable adhesive film for use in a wound dressing which is formed by solvent coating a swelled solid microsphere adhesive onto a backing at a coating weight effective for permitting particle to particle discontinuities to form between microspheres in the adhesive layer as the swelled microspheres shrink due to evaporation of the solvent.

These tapes advantageously maintain a relatively normal moisture content of the outermost skin layers so that any fractures in the skin caused by removal of the wound dressing tape will develop near the surface of the naturally desquamating layers of the stratum corneum. However, such tapes tend to lack sufficient initial adhesion to the skin and frequently fall off. In addition, such tapes typically exhibit significant build-up of adhesion which counteracts the reduced trauma benefit achieved from the enhanced breathability of the tape.

In summary, the prior art offers a choice between aggressive adhesive tapes which result in significant injury to the skin upon removal and minimally aggressive adhesive tapes that allow for moisture transmission but are prone to premature release from the skin. Consumer preference has resulted in most conventional adhesive tapes using the minimally aggressive adhesives.

Hence, a substantial need exists for a moisture vapor transmissive, low trauma wound dressing tape exhibiting good initial adhesion and minimal build-up of adhesion.

SUMMARY OF THE INVENTION

We have discovered a low trauma wound dressing possessing the advantageous combination of improved moisture vapor permeability, acceptable initial adhesion, minimal build-up of adhesion and effective antimicrobial performance. The wound dressing includes a moisture-vapor permeable backing and a contiguous particulate adhesive layer. The adhesive is comprised of tacky, substantially solvent-insoluble, solvent-dispersible, acrylate-based, elastomeric, pressure-sensitive adhesive microspheres. The adhesive may optionally be impregnated with an antimicrobial system of an antimicrobial agent and a transfer agent wherein the transfer agent is effective for allowing migration of the antimicrobial agent from the interior of the adhesive layer to the surface of the adhesive layer in contact with the wound.

DETAILED DESCRIPTION OF THE INVENTION INCLUDING A BEST MODE

DEFINITIONS

As utilized herein, including the claims, the term "critical micelle concentration" means the minimum concentration of emulsifier necessary for formation of the submicroscopic aggregation of emulsifier molecules known as micelles. It is understood that the critical micelle concentration is dependent upon the specific emulsifier used and the aqueous environment into which the emulsifier is placed. Generally, critical micelle concentrations will range from about 0.0001 to 3.0 moles/liter.

As utilized herein, including the claims, the phrase "contiguous particulate adhesive layer" means a particle containing adhesive layer (such as a microsphere adhesive) which is coated onto a surface at a particulate density such that the particles form a substantially contiguous surface over the entire coated surface with substantially all particles in physical contact with several other particles in the adhesive layer. Adhesive layers having minimal particle to particle contact, such as described in Silver (U.S. Pat. No. 3,691,140), and those which are pattern coated, such as disclosed in European Patent Application 353972, are not contiguous particulate adhesive layers.

As utilized herein, including the claims, the phrase "solvent insoluble" means that the compound is sparingly dissolved on a molecular level in the specified solvent.

As utilized herein, including the claims, the phrase "solvent swellable" means that the compound expands in size when contacted by the specified solvent and forms a dispersion when immersed in the solvent which consisting substantially of individual particles.

COMPOSITION

Wound Dressing Backings

Substrates suitable for use in the manufacture of a wound dressing intended for attachment to the skin include woven, nonwoven and knit fabrics and conformable synthetic polymeric films. Suitable polymeric films are those formed of such polymers as polypropylene, polyethylene, polyvinyl chloride, polyurethane, polyetheramide, polyester, and ethyl cellulose. Preferred synthetic films are those of the moisture vapor permeable type.

Suitable woven and nonwoven fabrics include those formed from threads of synthetic or natural materials including cotton, nylon, rayon, polyester, and the like. Synthetic fabrics suitable for use are those constructed from fibers having a tensile modulus of less than about 400,000 psi, preferably less than about 300,000 psi, measured in accordance with ASTM D-638. The fabric should be sufficiently continuous to prevent pathogens as large as a single cell, such as bacteria, from entering the wound.

Suitable substrates are moisture vapor permeable so as to permit the evaporation of body fluids, such as perspiration and wound exudate, from underneath the dressing. Preferred materials are those which possess a twenty four hour moisture vapor transmission rate ($MVTR_{up}$) of at least about 500 $g/m^2/24$ hours, most preferably at least about 1000 $g/m^2/24$ hours when measured in accordance with ASTM E 96-80 at 40° C. with a humidity differential of 80%. Preferred substrates also permit visual inspection of the wound without removal of the dressing.

A superior backing possessing the desired attributes of conformability, continuity, strength and moisture vapor permeability is a film of hydrophilic polyurethane with a thickness of from about 15 to 80 microns, preferably 20 to 60 microns, and most preferably 25 to 50 microns.

A continuous film of polyurethane sold by B. F. Goodrich under the trademark "Estane™" and a continuous film of polyester sold by E. I. Dupont de Nemours sold under the trademark "Hytrel™" each have an acceptable $MVTR_{up}$ value of about 1000 to 1500 $g/m^2/24hrs$. Woven substrates, such as that used by Minnesota Mining and Manufacturing Company in the construction of "Durapore™" surgical tape possess even higher $MVTR_{up}$.

Adhesive

The pressure-sensitive adhesives of the invention comprise at least about 70 wt % solid or hollow microspheres and optionally about 1 wt % to 30 wt % of a binder. Preferably, those formulations which do not include an antimicrobial agent comprise hollow microspheres admixed with a solvent-soluble, macromonomer-containing binder copolymer.

The major component of the adhesive microspheres is a hydrophobic acrylate monomer which contributes to the visco-elastic properties of the copolymer. The monomer is selected from the group consisting of (i) an acrylate or methacrylate ester of a non-tertiary $C_{4-12}$ alcohol, and (ii) an acrylate or methacrylate ester of a mixture of non-tertiary $C_{1-14}$ alcohols with an average of between about 4–12 carbon atoms per alcohol molecule. Such acrylate and methacrylate alcohol esters are generally oleophilic, water emulsifiable monomers having restricted water solubility. The homopolymers of these acrylate and methacrylate alcohol esters generally have glass transition temperatures below about –20° C.

Useful acrylate and methacrylate alcohol esters include specifically, but not exclusively, the acrylic acid and methacrylic acid esters of 1-butanol, 1-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, and 1-dodecanol. Mixtures of these alcohols are available from Exxon under the Exxal family mark. A preferred alcohol mixture for use in synthesizing the acrylate monomer is Exxal™-8.

Specific acrylate and methacrylate monomers include n-butyl acrylate, sec-butyl acrylate, 2-methyl butyl acrylate, 4-methyl-2-pentyl acrylate, 2-ethyl hexyl acrylate, isooctyl acrylate, isononyl acrylate, isoamyl acrylate, isodecyl acrylate, and isodecyl methacrylate.

Other vinyl monomers which have a homopolymer glass transition temperature of greater than about –20° C. may be included with the acrylate or methacrylate alcohol ester provided that the glass transition temperature of the resultant polymer is below about –20° C. Examples of suitable vinyl monomers include specifically, but not exclusively, tert-butyl acrylate, isobornyl acrylate, n-butyl methacrylate, isobutyl methacrylate, tert-butyl methacrylate, vinyl acetate, and acrylamide.

A first optional monomer is a polar monomer which is copolymerizable with the other monomers used to form the adhesive microspheres. Representative examples of suitable polar monomers include moderately ionized compounds such as acrylic acid, methacrylic acid, itaconic acid, crotonic acid, maleic acid, fumaric acid and sulfoethyl methacrylate; and ionic monomers such as sodium methacrylate, ammonium acrylate, sodium acrylate, trimethylamine p-vinylbenzimide, 4,4,9-trimethyl-4-azonia-7-oxo-8-oxa-9-decene-1-sulphonate, N,N-dimethyl-N-(β-methacryloxyethyloxyethyl) ammonium propionate betaine, trimethylamine methacrylimide, 1,1-diethyl-1-(2,3-dihydroxypropyl)amine methacrylimide, acrylonitrile, methacrylonitrile and maleic anhydride. The preferred polar monomers are the monocarboxylic and dicarboxylic acids and salts thereof.

The microspheres can include up to about 25 wt % polar monomers—based upon the total weight of all monomers in the polymer—with a loading of about 1 to 10 wt % preferred. Such loading provides microspheres with balanced pressure-sensitive adhesive properties. Inclusion of greater than about 25 wt % tends to produce an adhesive with insufficient tack and poor pressure sensitive adhesive performance.

A second optional monomer is an N-vinyllactam which is copolymerizable with the other monomers used to form the adhesive microspheres. Inclusion of this monomer reinforces the adhesive and contributes improved cohesiveness to the microspheres. Preferred N-vinyllactams are N-vinylpyrrolidone and N-vinyl-2-caprolactam.

The microspheres can include up to about 25 wt % of an N-vinyllactam monomer—based upon the total weight of all monomers in the polymer—with a loading of about 3 to 15 wt % preferred. Inclusion of greater than about 25 wt % tends to produce an adhesive with reduced tack and reduced conformability.

A third optional monomer is a hydrophilic alkylene oxide acrylate. The synthesis of such alkylene oxide acrylates employs commercially available starting materials and widely known and accepted conventional techniques such as described in U.S. patent application Ser. No. 84/00506 and International Patent Publication WO 84/03837. For example, the alkylene oxide acrylate monomer may be prepared by reacting an α, β-unsaturated carboxylic acid, such as acrylic acid or methacrylic acid, with an equimolar amount of a monoalcohol of a poly(lower alkylene oxide). The esterification reaction is generally conducted under anhydrous conditions in an organic solvent, such as toluene, which preferably forms an azeotropic mixture with the water generated by the esterification reaction. Typically, the alcohol is combined with the organic solvent and the unsaturated carboxylic acid is added to the alcohol/solvent mixture.

The reaction is conventionally conducted in the presence of an acid catalyst, such as para-toluenesulfonic acid, and a free-radical inhibitor, such as copper powder. The reaction mixture is refluxed for several hours under a nitrogen atmosphere and the resultant water removed by azeotropic distillation.

Suitable poly(alkylene oxides) which may be used to prepare the alkylene oxide acrylate monomers using the above-described procedure include Carbowax™ 350, Carbowax™ 550, Carbowax™ 750, Carbowax™ 2000 and Carbowax™ 5000 commercially available from Union Carbide Corp. The Carbowax™ family of monomers are methoxy-poly(ethylene oxide) ethanols possessing an average molecular weight expressed by the numeral provided in conjunction with the Carbowax™ mark (i.e.. Carbowax™ 5000 has an average molecular weight of five thousand). The poly(alkylene oxide) of choice is poly(ethylene oxide) having an average of from 3 to 40 poly(ethylene oxide) (EO) units, preferably 5 to 20 EO units, per molecule; including Carbowaxes™ 350, 550 and 750.

A suitable commercially available poly(alkylene oxide) acrylate ester is NK-Ester AM-90G™ available from Shin-Nakamura.

The microspheres can include up to about 15 wt % of a hydrophilic alkylene oxide acrylate monomer—based upon the total weight of all monomers in the polymer—with a loading of about 3 to 10 wt % preferred. Inclusion of greater than about 15 wt % tends to produce an adhesive having reduced tack.

The microspheres can be synthesized as either hollow or solid spheres. The microspheres are normally tacky, elastomeric, solvent dispersible and insoluble—but swellable—in organic solvents. Individual spheres generally have a diameter of at least 1 micrometer with diameters of about 1 to about 250 micrometers preferred. A majority of the hollow-type microspheres prepared by the methods of this invention have at least one void that has a diameter of at least about 10% the diameter of the microsphere, with void diameters of up to 30% readily achievable although larger void diameters are obtainable.

The adhesive may optionally include a minor amount of a binder copolymer. Suitable binder copolymers are those containing repeating units of the A and B monomers described below. The binder copolymer may optionally include the C monomer also described below.

Monomer A is a hydrophobic acrylate monomer of the same type which forms the major constituent of the microspheres. The acrylate monomer contributes to the viscoelastic properties of the binder copolymer. Briefly, the monomer is selected from the group consisting of (i) an acrylate or methacrylate ester of a non-tertiary $C_{4-12}$ alcohol, and (ii) an acrylate or methacrylate ester of a mixture of non-tertiary $C_{1-14}$ alcohols with an average of between about 4–12 carbon atoms per alcohol molecule.

The binder copolymer can include about 50 to 98 wt %, preferably about 85 to 95 wt %, monomer A—based upon the total weight of all monomers in the copolymer.

Monomer B is a polar monomer copolymerizable with the monomeric acrylic acid ester and of the same type described as an optional component of the microspheres.

The binder copolymer can include about 1 to 20 wt %, preferably about 1 to 15 wt %, monomer B—based upon the total weight of all monomers in the copolymer.

Monomer C has the general formula $X-(Y)_n-Z$ wherein: X is a vinyl group copolymerizable with the A and B monomers; Y is a divalent linking group; n is zero or one; and Z is a monovalent polymeric moiety having a $T_g$ greater than 20° C., an average molecular weight of between about 2,000 to 30,000, and is essentially unreactive under copolymerization conditions. The vinyl group of the C monomer is copolymerizable with the A and B monomers to form an elastomeric backbone having the polymeric moieties pendant therefrom.

The preferred C monomer has an X group of the general formula:

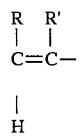

wherein: R is hydrogen or a COOH group and R' is hydrogen or methyl.

The double bond between the carbon atoms provides a copolymerizable moiety capable of copolymerizing with the A and B monomers.

The preferred C monomer has a Z group of the general formula:

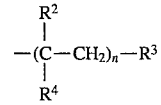

wherein:
n is an integer from 20 to 500,
$R^2$ is hydrogen or a lower alkyl,
$R^3$ is a lower alkyl, and
$R^4$ is a monovalent radical $CO_2R^5$ or

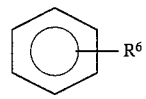

wherein: $R^5$ is a lower alkyl and $R^6$ is hydrogen or lower alkyl.

Preferably the C monomer has a general formula selected from the group consisting of

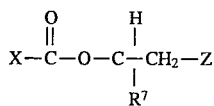

and

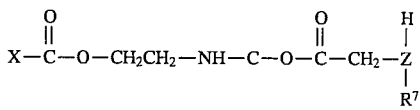

wherein $R^7$ is hydrogen atom or lower alkyl.

The vinyl terminated polymeric monomers are sometimes known as macromolecular monomers or macromonomers. Such monomers are well known and may be prepared by the method disclosed in U.S. Pat. Nos. 3,786,116 and 3,842,059 issued to Milkovich et al. The disclosures of the Milkovich et al. Letters Patent are incorporated herein by reference.

The binder copolymer can include about 1 to 30 wt %, preferably about 2 to 10 wt %, monomer C—based upon the total weight of all monomers in the copolymer.

The combination of B and C monomers in the copolymer should be within the range of about 2 to 50 wt % based upon the total weight of all monomers in the copolymer.

A polymeric suspension stabilizer may optionally be incorporated into the aqueous suspension to facilitate formation of the microspheres. The use of a polymeric suspension stabilizer is particularly useful where homopolymer microspheres are formed without the presence of an ionic copolymer. Many ionic and nonionic polymeric suspension stabilizers are effective for use in preparation of the microspheres. For example, polymeric stabilizers, such as those listed in U.S. Pat. No. 4,166,152 and incorporated herein by reference, would be useful suspension stabilizers according to the present invention. Polymeric stabilizers disclosed in U.S. Pat. No. 4,166,152 include, but are not limited to; polyoxyethylene, polyacrylic acid, polymethacrylic acid, polyacrylamide, poly(N-vinylpyrrolidone), polyethylene imine, polyvinyl methyl ether, salts thereof, and mixtures thereof.

Typically, stabilizer concentrations of greater than about 10 wt %—based on the monomers present in the suspension—tend to provide less than optimum properties to the resultant suspension. While certain stabilizers may function satisfactorily at concentrations of greater than 10 wt %—based upon the monomers present in the suspension— concentrations of greater than about 10 wt % generally tend to produce excessive amounts of undesirable latex in the polymerized suspension, interfere with control of final particle size, and result in microspheres having reduced tack.

Exemplary polymeric suspension stabilizers include (i) neutralized polycarboxylic acids including polyacrylic acid salts having a molecular weight of greater than about 5000 such as ammonium polyacrylate, sodium polyacrylate, lithium polyacrylate, and potassium polyacrylate; (ii) acrylamides including carboxyl modified polyacrylamides such as Cyanamer™ A-370 available from American Cyanamid; (iii)copolymers of acrylic acid and dimethylaminoethyl methacrylate; (iv) quaternary amines such as Gafquat™ (a quaternized poly(N-vinylpyrrolidone)) copolymer available from General Aniline) and JR™-400 (a quaternized amine substituted cellulosic available from Union Carbide); (v) crosslinked polyvinyl alcohols; and (vi)carboxy modified cellulosics such as Nateosol™ CMC Type 7L (a sodium carboxymethylcellulose available from Hercules). Set forth below is a table indicating representative stabilizers and the concentration level found to be effective for successful microsphere preparation.

TABLE ONE

| Trade Name | Class | [Interfacial Tension[1] (dynes/cm)] | Preferred Level (wt %) |
| --- | --- | --- | --- |
| None | 50/50 copolymer of acrylic acid and dimethylaminoethyl methacrylate | 21.2 | 1.0 |
| GOOD RITE K714 | Polyacrylic acid (neutralized with ammonia) | 21.0 | 1.0 |
| GAF GAFQUAT 755 | Quaternized poly(N-vinyl) pyrrolidone copolymer | 18.2 | 1.0 |
| UNION CARBIDE JR-400 | Quaternized cellulosic | 18.5 | 1.0 |
| CYANAMER A-370 | Carboxyl modified polyacrylamide | 21.0 | 3.0 |
| NATROSOL CMC Type 7L | Sodium carboxymethylcellulose | 19.8 | 5.0 |
| GANTREZ HYM | Copolymer of polyvinylmethyl ether and maleic anhydride (neutralized with ammonia) | 15.4 | 1.0 |

Antimicrobial System

An antimicrobial system may optionally be incorporated into the pressure-sensitive adhesive for purposes of reducing the likelihood that infectious microbes will be introduced through the wound covered by the wound dressing. A suitable antimicrobial system includes a pharmaceutically acceptable, topical antimicrobial agent and a transfer agent. The antimicrobial agent destroys or otherwise hinders growth and reproduction of pathogenic microbes while the transfer agent permits the antimicrobial agent to migrate from the interior of the adhesive layer to the exposed surface where it can contact and control pathogens before they are introduced into the wound.

Suitable antimicrobials include any of the pharmaceutically acceptable antimicrobial agents approved for topical application to open sores and wounds. The antimicrobial agent should also be compatible with the other constituents of the adhesive composition. Examples of suitable antimicrobial agents include OTTASEPT® (chloroxylenol available from the Bedford Chemicals Division of Ferro Corporation); SUMQUAT® 6020 (cetyl dimethyl ethyl ammonium bromide available from the Chemical Products Division of Hexcel Corporation); SUMQUAT® 6030 (cetyl trimethyl ammonium bromide available from the Chemical Products Division of Hexcel Corporation); SUMQUAT® 6110 (myristyl trimethyl ammonium bromide available from the Chemical Products Division of Hexcel Corporation); TCC® BACTERIOSTAT (3,4,4'-trichlorocarbanilide available from Monsanto Company); chlorhexidine gluconate, iodine, lauricidin, triclosan, and the like. Because of its superior compatibility with the other components in the adhesive composition, limited adverse effect upon the other desired properties and characteristics of the adhesive, and exceptional antimicrobial performance, the antimicrobial agent of choice is chlorhexidine gluconate.

Suitable transfer agents should facilitate migration of the antimicrobial agent from the interior volume of the adhesive layer to the surface of the adhesive layer in contact with the wound. Without intending to be unduly limited thereby, it is believed that transfer agents of the type described herein facilitate movement of the antimicrobial agent to the exposed surface of the adhesive layer by softening or plasticizing the adhesive composition and thereby permitting limited leaching of the antimicrobial to the surface of the adhesive layer.

Suitable transfer agents include aliphatic, aromatic and cyclic hydrocarbons having at least one pendant hydroxyl group such as glycerin, poly(alkylene oxides), alkoxylated sucrose, alkoxylated glycerol, nonyl phenol, octyl phenol, and the like. Because of its low cost, ease of availability, superior compatibility with the other components in the adhesive composition, limited deleterious effect upon the other desired properties and characteristics of the adhesive, and exceptional performance in facilitating migration of the antimicrobial agent to the surface of the adhesive layer, the transfer agent of choice is glycerine.

The adhesive composition can include about 0.5 to 5 wt % of the antimicrobial agent and about 5 to 30 wt % of the transfer agent—based upon the total weight of all components in the adhesive. While dependent upon the type of antimicrobial agent used, a loading of less than about 0.5 wt % antimicrobial agent is generally ineffective for controlling microbial growth at the site of the wound while a loading of greater than about 5 wt % antimicrobial agent tends to adversely affect the other desired properties and characteristics of the adhesive with little increase in the antimicrobial effectiveness of the adhesive. Similarly, dependent upon the specific transfer agent used, a loading of less than about 5 wt % transfer agent is generally ineffective for allowing the antimicrobial agent to migrate towards the surface of the adhesive layer to an extent sufficient to control microbial growth for extended periods of time, while a loading of greater than about 30 wt % transfer agent tends to adversely affect esters commercially available from various companies including the Foral™ and Pentalyn™ families of rosin esters available from Hercules, Inc. Specific tackifiers acceptable for use in the adhesive of the invention include Foral™ 65, Foral™ 85 and Foral™ 105. Other useful tackifiers include those based on t-butyl styrene disclosed in U.S. Pat. No. 5,045,569. Suitable plasticizers include the widely available plasticizers dioctyl phthalate, 2-ethyl hexyl phosphate, and tricresyl phosphate.

It is also within the scope of this invention to include various other biocompatible components, such as pigments, fillers, stabilizers, rheological modifiers, and various polymeric additives.

Release Liner

The release liner may be any of the commercially available paper and film liners which have been treated to provide a release surface (such as a surface coating of an aliphatic fluorochemical or silicone) having acceptable handling characteristics (such as limited transfer of adhesive to the liner).

MANUFACTURE

Adhesive

Aqueous suspensions of hollow microspheres may be prepared by a "two-step" emulsification process. The first step involves formation of a water-in-oil emulsion by combining an aqueous solution of the polar monomer(s) and an oil-phase emulsion of the other monomer(s) (i.e., the acrylate or methacrylate alcohol ester) emulsified by an emulsifier having a low hydrophilic-lipophilic balance (HLB) value. In those situations where a polar monomer is not included in the microsphere, water may be mixed directly into the oil phase to form the water-in-oil emulsion.

Suitable emulsifiers are those having an HLB value below about 7, with preferred emulsifiers having an HLB value of about 2 to 7. Emulsifiers having an HLB value of greater than about 7 tend to produce an oil-in-water emulsion rather than the desired water-in-oil emulsion. Examples of suitable emulsifiers are the anionic emulsifiers of sorbitan monoleate, sorbitan trioleate, and ethoxylated oleyl alcohol, such as BRIJ™ 93, available from Atlas Chemical Industries, Inc.

The other components, such as the free radical initiator and any crosslinking monomer, are dissolved in the oil-phase, along with the oil-phase monomers, prior to formation of the oil-in-water emulsion.

A thickening agent, such as methyl cellulose, may be incorporated into the aqueous phase, prior to formation of the water-in-oil emulsion.

The second step involves formation of a water-in-oil-in-water emulsion by dispersing the water-in-oil emulsion formed in the first step into a second aqueous-phase containing a second emulsifier having an HLB value above about 6. The second aqueous phase may contain that portion of the polar monomer(s) which was not incorporated into the water-in-oil emulsion with the first aqueous-phase.

Emulsifiers suitable for use in forming the water-in-oil-in-water emulsion of this invention are those having an HLB value of greater that about 6. Emulsifiers having an HLB value of less than about 6 tend to produce an oil-in-water emulsion rather than a water-in-oil emulsion with the disadvantage discussed infra. Examples of suitable emulsifiers include ethoxylated sorbitan monoleate, ethoxylated lauryl alcohol, and alkyl sulfates.

The emulsifier used in both steps should be incorporated at a concentration which is greater than its critical micelle concentration. Additional details concerning the preparation of multiple emulsions, such as the water-in-oil-in-water emulsions used herein, may be found in various literature references, including *Surfactant Systems: Their Chemistry, Pharmacy-& Biology*, (D. Attwood and A. T. Florence, Chapman & Hall Limited, New York, New York, 1983). Heat and/or radiation is then applied to the water-in-oil-in-water emulsion to initiate polymerization of the monomers.

Following polymerization, an aqueous suspension of hollow microspheres is obtained which is stable to agglomeration or coagulation under room temperature conditions. The suspension may have a non-volatile solids contents of from about 10 to about 70 wt %. Upon prolonged standing, the suspension separates into two phases, one phase being aqueous and substantially free of polymer, the other phase being an aqueous suspension of microspheres. Both phases may contain a minor portion of small latex particles. Decantation of the microsphere-rich phase provides an aqueous suspension having a nonvolatile solids content on the order of 40–50 wt % which, if shaken with water, will readily redisperse. This aqueous suspension of microspheres may be utilized without further treatment.

Alternatively, the aqueous suspension may be coagulated with a coagulating agent, washed and than dried to form dry microspheres. Suitable coagulating agents include (i) polar organic solvents, such as methanol, isopropanol and the like, (ii) ionic emulsifiers having a charge opposite to that of the emulsifier used in the polymerization process, and (iii) saturated salt solutions. The dried microspheres can be readily dispersed in common organic liquids, such as ethyl acetate, tetrahydrofuran, heptane, 2-butanone, benzene, cyclohexane, and various esters. It is, however, not possible to readily resuspend them in water.

Aqueous suspensions of solid microspheres may also be prepared by a "one-step" emulsification process. The one-step process is conducted by aqueous suspension polymerization of (i) at least one alkyl acrylate, alkyl methacrylate, and/or vinyl ester monomer, (ii) at least one free radically reactive hydrophilic monomer, (iii) at least one polymeric suspension stabilizer, such as polyvinyl alcohol, and (iv) an optional polar monomer. It is believed that other polymeric suspension stabilizers, such as the neutralized polycarboxylic acids described previously herein and in U.S. Pat. No. 4,166,152, issued to Baker et al., and other steric or electrosteric polymeric stabilizers could also be usefully incorporated into the microspheres. Suitable polymeric suspension stabilizers include specifically, but not exclusively, one or more of polyoxyethylene, poly(N-vinylpyrrolidone), polyethyleneimine, poly(vinyl methyl ether), and salts thereof.

The methods described herein may be modified by withholding the addition of all or a portion of the free radically reactive hydrophilic monomer(s) and/or the polar monomer(s) until after polymerization of the oil emulsion is initiated. This alternative procedure may be used provided the withheld components are added to the polymerizing mixture prior to complete polymerization of the monomers in the water-in-oil emulsion. According to this alternative procedure, the formulator may add any portion of the free radically reactive hydrophilic monomer(s) and/or polar monomer(s) at any convenient point in preparing the pressure-sensitive adhesive microspheres.

In addition to the processes described hereinabove, microspheres can be prepared according to the processes described in U.S. Patent Nos. 5,053,436 and 5,045,569 and European Patent Application WO 94/13751, the descriptions of which are incorporated herein by reference.

Polymerization of the emulsified monomers is effected by standard free radical polymerization utilizing a suitable free radical initiator. Suitable initiators are those which are both fairly oil-soluble and fairly water-insoluble. Use of a water-soluble polymerization initiator tends to cause the formation of excessive amounts of latex which—due to its small particle size—tends to destroy the desired properties and characteristics of the microspheres.

Numerous suitable free radical initiators are well known in the industry. Preferred free radical initiators are those which are freely soluble in oil with limited water solubility. Exemplary of those free radical initiators suitable for use in the present invention are those described in U.S. Pat. No. 4,994,322 and such description is incorporated herein by reference. Suitable thermally activated initiators include specifically, but not exclusively: azo compounds such as 2,2'-azo-bis(isobutyronitrile); and hydroperoxides and peroxides such as tert-butyl hydroperoxide, benzoyl peroxide, and cyclohexanone peroxide. Suitable photoinitiators include specifically, but not exclusively, benzophenone, benzoin ethyl ether and 2,2-dimethoxy-2-phenylacetophenone.

The concentration of initiator may affect sphere quality and should be carefully monitored. Generally, about 0.15 to 0.70 wt %, preferably about 0.25 to 0.5 wt %, initiator—based upon the total weight of all monomers—is effective for initiating polymerization and providing superior quality microspheres. Initiator concentrations below about 0.15 wt % tend to result in slow polymerization rates while concentrations of greater than about 0.70 wt % tend to increase the rate of polymerization and thereby complicate control of the exothermic reaction.

The suspension from which the microspheres of the invention are made may also contain a multifunctional crosslinking agent. The term "multifunctional", as used herein, refers to crosslinking agents which possess two or more free radically polymerizable ethylenically unsaturated groups. Useful multifunctional crosslinking agents include (i) acrylic or methacrylic diol esters such as butanediol diacrylate, decanediol diacrylate and hexane diol diacrylate; (ii) acrylic triol esters such as glycerol triacrylate, and (iii) acrylic tetrol esters such as pentaerythritol tetracrylate. Other useful crosslinking agents include (iv) polymeric multifunctional (meth)acrylates such as poly(ethylene oxide) diacrylate and poly(ethylene) oxide dimethacrylate; (v) polyvinylic crosslinking agents such as substituted and unsubstituted divinylbenzene; and (vi) difunctional urethane acrylates, such as Ebecryl™ 270 (a mixture of acrylated urethanes with a resultant average molecular weight of 1500 available from Radcure Specialties) and Ebecryl™ 230 (a mixture of acrylated urethanes with a resultant average molecular weight of 5000 available from Radcure Specialties).

The crosslinker can be added to the suspension at any time prior to complete polymerization. The crosslinker is preferably added prior to initiation of polymerization.

The crosslinker may be incorporated at a level of up to about 0.15 equivalent wt %, preferably up to about 0.1 equivalent wt %—based upon the weight of the total polymerizable composition. The term "equivalent wt %" of a given compound is defined as the number of equivalents of that compound divided by the total number of equivalents in the total composition wherein an equivalent is the number of grams divided by the equivalent weight. The term "equivalent weight" is defined as the molecular weight divided by the number of polymerizable groups in the monomer (in the case of those monomers with only one polymerizable group, equivalent weight=molecular weight).

Microspheres formed solely from a methacrylate monomer generally require the inclusion of a crosslinking agent. Failure to include a crosslinking agent in such cases can result in the synthesis of solvent soluble microspheres.

The binder copolymer can be prepared by standard free radical polymerization of the A, B and optional C monomers. Such techniques are further described in D. Satas, *Handbook of PSA Technology*, 2nd Ed., p. 908, Van-Norstrand-Rheinhold, New York, 1989. The relevant disclosures of these references are hereby incorporated by reference.

The antimicrobial system may be conveniently formed and uniformly dispersed throughout the adhesive composition by simply blending the antimicrobial agent into the transfer agent and then introducing the blend into the adhesive composition. Alternatively, the antimicrobial agent and transfer agent may be independently blended into the adhesive composition with sufficient agitation to ensure dispersion of the antimicrobial agent throughout the adhesive composition.

The pressure-sensitive adhesive of the invention may be made by combining a dispersion of microspheres with a solution of the binder copolymer at a dry weight ratio of microspheres to binder of about 2:1 to 100:1 with a preferred weight ratio of about 3:1 to 10:1. When employed, the antimicrobial system is preferably incorporated into the adhesive composition so as to provide about 0.5 to about 5 wt % antimicrobial agent—based upon the total weight of all other components in the adhesive composition, including transfer agent. Concentrations of about 5 to about 30 wt % transfer agent—based upon the total weight of all other components in the adhesive composition, including transfer agent—have been found to be effective for producing the necessary level of surface migration without significantly impacting the other desired attributes of the adhesive.

Since the adhesive is intended for use in a wound dressing, the adhesive should be sterilized. A widely accepted method of sterilizing wound dressings is to subject the dressing to about 25 to 50 kilograys of gamma radiation. The wound dressing may also be sterilized by the ethylene oxide sterilization method.

Wound Dressing Tape

Solvent-based adhesive compositions can be coated onto the substrate by any of a variety of conventional techniques such as roll coating, spray coating, extrusion coating, coextrusion, hot-melt coating and the like. The process of choice depends upon the nature of the substrate employed. For example, a preferred method for coating the adhesive upon a nonwoven fabric is to disperse the adhesive copolymer microspheres in an organic solvent, spread the dispersed copolymer onto a release liner, and then laminate the adhesive coating onto the nonwoven fabric before the adhesive is completely dry. Alternatively, the adhesive microspheres can be coated directly from water.

Application

The dressing may be easily applied by simply removing the release liner and applying the exposed adhesive-containing surface over the wound.

PROPERTIES & CHARACTERISTICS

Moisture Vapor

Transmission Rate

The wound dressings of this invention possess a superior moisture vapor transmission rate which permits the evaporation of perspiration and wound exudate from underneath the dressing. Preferred adhesives for use in the dressing are those with a moisture vapor transmission rate ($MVTR_{up}$) of at least about 500 g/m²/24 hours, most preferably at least about 1000 g/m²/24 hours, when measured in accordance with ASTM E 96-80 at 40° C. with a humidity differential of 80%.

Skin Adhesion

The adhesives used in this invention exhibit an initial skin adhesion ($T_O$) of between about 0.01 to about 0.2 N/cm width, preferably between about 0.03 to about 0.15 N/cm width; and a twenty four hour skin adhesion ($T_{24}$) of between about 0.07 to about 0.5 N/cm width, preferably between about 0.15 to about 0.3 N/cm width. Adhesives with an adhesion of less than about 0.01 N/cm width at any time during normal periods of use tend to peel prematurely from the skin while adhesives with an adhesion of greater than about 0.5 N/cm width at the time of removal will frequently produce significant skin irritation upon removal despite effective evaporation of fluids from beneath the dressing.

Microbial Control

The wound dressings of this invention which include the optional antimicrobial system also provide effective antimicrobial properties to the exposed surface of the wound covered by the dressing. The antimicrobial-containing adhesive compositions of this invention are effective for achieving a 2.5 to 6 log reduction in bacteria as tested in accordance with the microbial assay described infra, with a log reduction of greater than about 2.5 generally considered effective for controlling the growth of bacteria under the dressing.

TESTING PROTOCOLS

Moisture Vapor

Transmission Rate (Upright)

The Moisture Vapor Transmission Rate ($MVTR_{up}$) is measured in accordance with ASTM E 96-80 as modified below.

Thirty five millimeter diameter samples of a 0.025 cm thick film of the adhesive is laminated to a 0.0275 cm thick polyurethane web having a $MVTR_{up}$ of 2,000 to 2,400 g/m²/24 hours measured at 40° C. and a relative humidity differential of 80%.

The laminated samples are sandwiched between the adhesive surfaces of two axially aligned foil adhesive rings having 2.54 cm diameter holes. Each sample is pulled to ensure a flat, wrinkle-free and void-free foil/sample/foil laminate.

A four-ounce (0.14 liters) glass jar is filled half-full with distilled water. The jar is fitted with a screw-on cap having a 3.8 cm diameter hole concentrically aligned with a rubber washer having a 4.445 cm outside-diameter and a 2.84 cm inside-diameter.

The foil/sample/foil laminate is concentrically positioned on the rubber washer and the sample-containing sub-assembly screwed loosely onto the jar.

The assembly is placed into a chamber maintained at a temperature of 40° C. and 20% relative humidity. The assembly is removed from the chamber after four hours, weighed to the nearest 0.01 gram ($W_1$), and immediately returned to the chamber. The cap is now screwed tightly onto the jar without bulging of the sample. The assembly is again removed from the chamber after an additional eighteen hours and weighed to the nearest 0.01 gram ($W_2$).

The $MVTR_{up}$ of the laminated samples (measured in grams of water transmitted per square meter of sample area over a twenty four hour period) may then be calculated according the formula set forth below:

$$MVTR_{up}=(W_1-W_2)(4.74\times10^4)/t$$

where:
 ($W_1$) is the initial weight of the assembly (grams)
 ($W_2$) is the final weight of the assembly (grams), and
 (t) is the time period between $W_1$ and $W_2$ (hrs).

Three samples of each adhesive were run and the average of the three samples reported.

Moisture Vapor

Transmission Rate (Inverted)

The protocol for measuring "Inverted" MVTR ($MVTR_{invt}$) is the same as the "Upright" protocol except that the assembly is inverted inside the chamber once the cap is tightly screwed onto the jar so that the water within the jar directly contacts the foil/sample/foil laminate while the assembly is within the chamber.

Skin Adhesion

Evaluation of the adhesiveness of an adhesive composition to human skin is an inherently temperamental but essentially reproducible determination so long as the conditions established below are observed. Human skin possesses wide variations in composition, topography, and the presence/absence of various body fluids. However, controlled and comparative values of adhesion are attainable by selecting a panel of individuals which is sufficiently large to provide statistically significant data and one or more evaluators trained to recognize the normal skin variations encountered in medical practice.

Initial skin adhesion ($T_O$) and skin adhesion after 24 hours of continuous contact with the skin ($T_{24}$) is measured in accordance with the widely accepted PSTC-1 Peel Adhesion Test for single coated adhesive tape conducted at a removal angle of 180°. The PSTC-1 Peel Adhesion Test is a testing protocol established by the Specifications and Technical Committee of the Pressure Sensitive Tape Council located at 5700 Old Orchard Road, Skokie, Ill. The test is modified for our purposes by applying the tape to the skin of a living human.

The adhesive is tested as a 0.025 mm film coated onto a 0.0275 mm thick polyurethane web having a $MVTR_{up}$ $T_{24}$ of 2,000 to 2,400 g/m²/24 hours measured at 40° C. and a relative humidity differential of 80%. Three samples measuring 2.5 cm wide by 7.6 cm long are applied to the back of each of six human subjects (three men and three women). The subjects are placed in a prone positioned with arms at their sides and heads turned to one side. Samples are applied to both sides of the spinal column with the length of each sample positioned at a right angle to the spinal column. The samples are applied without tension or pulling of the skin.

The samples are pressed into place with a 2 kg roller moved at a rate of approximately 2.5 cm/sec with a single forward and reverse pass. No manual pressure should be applied to the roller during application.

The samples are then removed either immediately after application ($T_O$) or after 24 hours of continuous contact with the skin ($T_{24}$), at a removal angle of 180° and removal rate of 15 cm per minute, using an adhesion tester equipped with 25 lb (11.4 kg) test line attached to a 2.5 cm clip. The clip is attached to the edge of the sample furthest from the spinal column by manually lifting about 1 cm of the sample from the skin and attaching the clip to the raised edge. The adhesion tester is a strain-gauge mounted on a motor-driven carriage.

The measured force exerted to effect removal is reported in Newtons per centimeter.

Microbial Assay

Culture plates are prepared from a solution of 3% BACTO agar, available from Difco Laboratories of Detroit, Mich., in distilled water. The plates are dried for 20–30 minutes at 37° C. in an incubator prior to use.

Onto a 25 millimeter diameter Gelman metricel filter having a 0.45 micrometer pore size is filtered five milliliters of a $3\times10^6$ CFU/ml suspension of Enterococcus feacalis. The contaminated filter is air dried and placed on the surface of one of the previously prepared culture plates.

A 1 ½=inch (3.81 cm) square sample of the wound dressing to be tested is prepared and placed into contact with the contaminated filter resting on the culture agar plate with the adhesive side of the wound dressing physically contacting the contaminated filter. The plates are then incubated for 30 minutes at 37° C. in an arid incubator after which the wound dressing and contaminated filter are removed.

The contaminated filter is submerged in 100 milliliters of a neutralizer and processed for three to five minutes in a Waring blender. The neutralizer is selected based upon the anti-microbial agent incorporated in the wound dressing adhesive with Difco Neutralizing Buffer used when the wound dressing includes chlorhexidine gluconate as the anti-microbial agent and 0.1 wt % sodium thiosulfate solution used when the wound dressing included iodine as the anti-microbial agent.

The processed samples are then diluted with phosphate buffered saline, plated onto an m-entococcus agar culture plate, and incubated at 37° C. for 24 hours, after which the number of bacterial colonies are counted and recorded.

EXPERIMENTAL

Experiment 1

Synthesis of Microspheres (Adhesives #1–19)

Into a one-liter resin reactor equipped with a mechanical stirrer, a condenser, and inlet-outlet lines was charged (i) 450 grams of deionized water, (ii) 6 grams of Standapol™ A (an ammonium lauryl sulfate emulsifier purchased from Henkel AG), (iii) 0.72 grams Lucidol™-70 (benzoyl peroxide purchased from Pennwalt Corporation), and (iv) 150 grams of a mixture of monomers isooctyl acrylate, isodecyl acrylate, acrylic acid, N-vinylpyrrolidone and poly(ethylene oxide) acrylate with the ratio of monomers specified in TABLE TWO and TABLE FOUR. This monomer suspension was homogenized in an Omni™ mixer (available from Omni International Inc.) prior to polymerization for adhesives 15 and 16. The mixture was then stirred at 400 rpm for the remainder of the polymerization reaction. The atmosphere in the reactor vessel was evacuated by application of vacuum and the vessel purged with argon through completion of the polymerization reaction. The temperature of the reactor was raised to between 55° and 65° C. and maintained at that elevated temperature for a time period specified in TABLE TWO for purposes of completing polymerization. The polymerized suspension was then allowed to cool to room temperature and the suspension removed from the reactor and filtered. Optical microscopy revealed microspheres with an average diameter reported in TABLE TWO suspended in water.

Experiment 2

Adhesive Testing (Adhesives #1–19)

The initial Moisture Vapor Transmission Rate (Upright) ($MVTR_{up}$), Skin Adhesion (Initial) ($T_{O'}$), and Skin Adhesion (Twenty Four Hours) ($T_{24}$) of the samples was then measured in accordance with the testing protocols set forth herein. The results of such testing are set forth in TABLE THREE below.

TABLE TWO

Adhesive Compositions

| Adhesive # | MONOMERS | | | | | Time/Temp Hr/°C. | Diameter ($\mu$) | Carrier |
|---|---|---|---|---|---|---|---|---|
| | IOA % | IDA % | AA % | NVP % | EOA % | | | |
| 1 | 94 | — | 6 | — | — | 2.5/65 | 39 | Isopropanol |
| 2 | 90 | — | — | 10 | — | 22/60 | — | — |
| 3 | — | 90 | — | 10 | — | 22/60 | — | — |
| 4 | 95 | — | — | 5 | — | 22/60 | — | — |
| 5 | 98 | — | 2 | — | — | 22/60 | 39 | Isopropanol |
| 6 | 90 | — | 5 | — | $5_{16}$ | 4/55 | — | Isopropanol |
| 7 | 90 | — | — | 5 | $5_{16}$ | 5/55 | — | Isopropanol |
| 8 | 98 | — | 2 | — | — | 22/60 | 39 | $H_2O$ |
| 9 | 98 | — | 2 | — | — | 22/60 | 74 | Isopropanol |
| 10 | 98 | — | 2 | — | — | 22/60 | 74 | $H_2O$ |
| 11 | 97.5 | — | 2.5 | — | — | 7.5/65 | — | Isopropanol |
| 12 | 97.5 | — | 2.5 | — | — | 7.5/65 | — | Isopropanol |
| 13 | 90 | — | 5 | — | $10_{16}$ | 4/55 | — | Isopropanol |
| 14 | 90 | — | — | 5 | $10_{16}$ | 5/55 | — | Isopropanol |
| 15 | 90 | — | — | 5 | $5_{16}$ | 5/55 | 2 | Isopropanol |
| 16 | 90 | — | 5 | — | $5_{16}$ | 5/60 | 2 | Isopropanol |
| 17 | 90 | — | — | 5 | $5_{16}$ | 5/65 | — | Isopropanol |
| 18 | 90 | — | — | 5 | $5_{16}$ | 5/60 | — | Isopropanol |
| 19 | 90 | — | — | 5 | $5_{16}$ | 5/60 | — | Isopropanol |

TABLE THREE

Adhesive Characteristics

| Example # | Adhesive # | Coating Weight (mg/cm²) | MVTR | w/o Sterilization | | Sterilized w/ Gamma Radiation | | |
|---|---|---|---|---|---|---|---|---|
| | | | | (N/cm) $T_0$ | (N/cm) $T_{24}$ | KiloGray | (N/cm) $T_0$ | (N/cm) $T_{24}$ |
| 110 | 1 | 1.55 | 1238 | 0.027 | 0.143 | — | — | — |
| 111 | 1 | 1.68 | 1093 | 0.039 | 0.243 | — | — | — |
| 113 | 1 | 2.78 | 639 | 0.050 | 0.174 | — | — | — |
| Tegaderm[1] | | | 700 | 0.151 | 0.529 | — | — | — |
| 120 | 2 | 0.75 | 1408 | 0.085 | 0.278 | 27 | 0.035 | 0.124 |
| 121 | 2 | 1.12 | 1257 | 0.151 | 0.614 | 27 | 0.081 | 0.236 |
| 122 | 2 | 1.50 | 1086 | 0.208 | 0.668 | 27 | 0.097 | 0.231 |
| 123 | 2 | 1.86 | 994 | 0.197 | 0.649 | 27 | 0.119 | 0.301 |
| Tegaderm[2] | | | | 0.162 | 0.456 | — | 0.143 | 0.494 |
| 130 | 3 | 0.46 | 1175 | — | — | 31 | 0.050 | 0.116 |
| 131 | 3 | 0.63 | 1179 | — | — | 31 | 0.085 | 0.170 |
| 132 | 3 | 0.84 | 992 | — | — | 31 | 0.077 | 0.197 |
| 133 | 3 | 1.05 | — | — | — | 31 | 0.120 | 0.216 |
| 134 | 3 | 1.63 | — | 0.097 | 0.066 | — | — | — |
| 135 | 3 | 2.26 | — | 0.166 | 0.293 | — | — | — |
| 137 | 3 | 2.97 | — | 0.279 | 0.371 | — | — | — |
| Tegaderm[3] | | | 700 | — | — | 31 | 0.166 | 0.579 |
| Micropore[3] | | | — | 0.189 | 0.421 | — | — | — |
| 140 | 4 | 0.59 | 1547 | — | — | 31 | 0.046 | 0.062 |
| 141 | 4 | 0.92 | 786 | — | — | 31 | 0.054 | 0.097 |
| 142 | 4 | 0.96 | 758 | — | — | 31 | 0.062 | 0.116 |
| 143 | 4 | 1.34 | 743 | — | — | 31 | 0.085 | 0.147 |
| 144 | 4 | 2.3–2.6 | 2126 | 0.093 | 0.097 | 34 | 0.039 | 0.073 |
| Tegaderm[4] | | | 700 | — | — | 31 | 0.197 | 0.541 |
| 150 | 5 | 0.59 | 1076 | — | — | — | 0.062 | — |
| 151 | 5 | 1.30 | 941 | — | — | 31 | 0.085 | — |
| 152 | 5 | 1.55 | 854 | — | — | 31 | 0.100 | — |
| 153 | 5 | 1.78 | 768 | — | — | 31 | 0.104 | — |
| 154 | 5 | 1.75–1.80 | 768 | 0.069 | 0.162 | — | — | — |
| 155 | 5 | | | 0.089 | 0.220 | — | — | — |
| Tegaderm[5] | | | 700 | — | — | 31 | 0.185 | — |
| 160 | 6 | 2.3–2.6 | 757 | 0.174 | 0.436 | — | — | — |
| 170 | 7 | 2.3–2.6 | 652 | 0.243 | 0.486 | — | — | — |
| 180 | 8 | 1.46 | — | 0.073 | 0.201 | — | — | — |
| 181 | 8 | 2.76 | — | 0.166 | 0.568 | — | — | — |
| 182 | 8 | 5.00 | — | 0.266 | 1.239 | — | — | — |
| 190 | 9 | 0.38 | 1123 | — | — | 31 | 0.027 | — |
| 191 | 9 | 0.63 | 1168 | — | — | 31 | 0.027 | — |
| 192 | 9 | 0.92 | 1113 | — | — | 31 | 0.039 | — |
| 193 | 9 | 1.05 | 1214 | — | — | 31 | 0.046 | — |
| 194 | 9 | | | 0.035 | — | — | — | — |

TABLE THREE-continued

| | | Coating | | Adhesive Characteristics | | | | |
| | | | | w/o Sterilization | | Sterilized w/ Gamma Radiation | | |
| Example # | Adhesive # | Weight (mg/cm²) | MVTR | (N/cm) $T_0$ | (N/cm) $T_{24}$ | KiloGray | (N/cm) $T_0$ | (N/cm) $T_{24}$ |
|---|---|---|---|---|---|---|---|---|
| Tegaderm[9] | | | 700 | — | — | 31 | 0.162 | — |
| 200 | 10 | 1.05 | — | 0.035 | — | — | — | — |
| 201 | 10 | 1.51 | — | 0.092 | 0.050 | — | — | — |
| 202 | 10 | 2.76 | — | 0.046 | 0.085 | — | — | — |
| 203 | 10 | 3.93 | — | 0.069 | 0.220 | — | — | — |
| 204 | 10 | 4.27 | — | 0.062 | 0.174 | — | — | — |
| Micropore[10] | — | — | — | 0.154 | 0.579 | — | — | — |
| 210 | 11 | 1.93 | — | 0.066 | 0.042 | — | — | — |
| 211 | 11 | 2.85 | — | 0.216 | 0.347 | — | — | — |
| 212 | 11 | 3.77 | — | 0.259 | 0.421 | — | — | — |
| 213 | 11 | 4.52 | — | 0.332 | 0.521 | — | — | — |
| 214 | 11 | 5.11 | — | 0.386 | 0.560 | — | — | — |
| Micropore[1] | | | | 0.185 | 0.568 | — | — | — |
| 250 | 15 | 2.50 | 790 | 0.205 | 0.546 | — | — | — |
| 260 | 16 | 2.50 | 847 | 0.143 | 0.494 | — | — | — |
| 270 | 17 | 2.26 | — | 0.019 | 0.166 | — | — | — |
| 280 | 18 | 2.18 | — | 0.027 | 0.124 | — | — | — |
| 290 | 19 | Coagulate | — | — | — | — | — | — |
| Tegaderm[2] | | | | | | — | 0.212 | 0.618 |

Experiment 3

Synthesis of Microspheres (Adhesives #20–40)

Into a one-liter resin reactor equipped with a mechanical stirrer, a condenser, and inlet-outlet lines was charged (i) 450 grams of deionized water, (ii) 6 grams of Standapol™ A (an ammonium lauryl sulfate emulsifier purchased from Henkel AG), (iii) 0.72 grams Lucidol™-70 (benzoyl peroxide purchased from Pennwalt Corporation), and (iv) 150 grams of a mixture of the monomers isooctyl acrylate, N-vinylpyrrolidone, acrylic acid, and poly(ethylene oxide) acrylate with the ratio of monomers specified in TABLE TWO and TABLE FOUR. This monomer suspension was homogenized in an Omni™ mixer (available from Omni International Inc.) prior to polymerization for adhesives 20, 23–26 and 32–36. The mixture was stirred at 400 rpm for the remainder of the polymerization reaction. The atmosphere in the reactor vessel was evacuated by application of vacuum and the vessel purged with argon through completion of the polymerization reaction. The temperature of the reactor was raised to between 55° and 65° C. and maintained at that elevated temperature for a time period specified in TABLE FOUR for purposes of completing polymerization. The polymerized suspension was then allowed to cool to room temperature and the suspension removed from the reactor and filtered. Optical microscopy revealed microspheres with an average diameter as reported in TABLE FOUR suspended in water.

The adhesive was formulated from the microspheres by including an antimicrobial system into the adhesive. The antimicrobial system included (i) an antimicrobial agent selected from chlorhexidine gluconate (TABLE FIVE) and iodine (TABLE SIX), (ii) a transfer agent selected from glycerol, Carbowax™ 200 and Carbowax™ 400 as set forth in TABLE FIVE and TABLE SIX, and (iii) the optional coating promoter poly(N-vinylpyrrolidone). The chlorhexidine gluconate was incorporated at a concentration of 4 parts chlorhexidine gluconate per 100 parts combination of microspheres, poly(N-vinylpyrrolidone) and glycerine. The iodine was incorporated at a concentration of 2 parts chlorhexidine gluconate per 100 parts combination of microspheres, poly(N-vinylpyrrolidone) and glycerine.

Experiment 4

Adhesive Testing (Adhesives #20–40)

The Skin Adhesion (Initial) ($T_{O'}$), Skin Adhesion (Twenty Four Hours) ($T_{24}$), and Log Bacteria Reduction of the samples was then measured in accordance with the testing protocols set forth herein. The results of such testing are set forth in TABLE FIVE and TABLE SIX below.

TABLE FOUR

| | Adhesive Compositions | | | | | | | | |
| | MONOMERS | | | | | Time/Temp | Diameter | | |
| Adhesive # | IOA % | IDA % | AA % | NVP % | EOA % | Hr/°C. | (μm) | Extract % | Carrier |
|---|---|---|---|---|---|---|---|---|---|
| 20 | 90 | — | — | 5 | $5_{16}$ | — | 2 | — | — |
| 21 | 90 | — | — | 5 | $5_{16}$ | — | 50 | — | — |
| 22 | 80 | — | — | 10 | $10_{16}$ | — | 55 | — | — |
| 23 | 90 | — | — | 5 | $5_{16}$ | — | 2 | — | — |
| 24 | 92 | — | — | 5 | $3_{16}$ | — | 2 | — | — |
| 25 | 93 | — | — | 5 | $2_{16}$ | — | 2 | — | — |
| 26 | 94 | — | — | 3 | $3_{16}$ | — | 2 | — | — |
| 27 | 90 | — | — | 5 | $5_9$ | — | 50 | — | — |
| 28 | 96 | — | — | 2 | $2_9$ | — | 55 | — | — |
| 29 | 94 | — | — | 3 | $3_9$ | — | 55 | — | — |
| 30 | 93 | — | — | 5 | $2_9$ | — | 55 | — | — |

TABLE FOUR-continued

| | Adhesive Compositions | | | | | | | | |
|---|---|---|---|---|---|---|---|---|---|
| | MONOMERS | | | | | Time/Temp | Diameter | | |
| Adhesive # | IOA % | IDA % | AA % | NVP % | EOA % | Hr/°C. | (μm) | Extract % | Carrier |
| 31 | 94 | — | — | 5 | $1_9$ | — | 55 | — | — |
| 32 | 90 | — | — | 5 | $5_9$ | — | 2 | — | — |
| 33 | 96 | — | — | 2 | $2_9$ | — | 2 | — | — |
| 34 | 94 | — | — | 3 | $3_9$ | — | 2 | — | — |
| 35 | 93 | — | — | 5 | $2_p$ | — | 2 | — | — |
| 36 | 94 | — | — | 5 | $1_p$ | — | 2 | — | — |
| 37 | 96 | — | 4 | — | — | — | 60 | — | — |
| 38 | 95 | — | — | 5 | — | — | 60 | — | — |
| 39 | 93 | — | 2 | 5 | — | — | 60 | — | — |
| 40 | 90 | — | 2 | 5 | 3 | — | 60 | — | — |

TABLE FIVE

Microbial Adhesive Chacteristics
CHLORHEXIDINE GLUCONATE

| Example # | Adhesive # | Transfer Agent Type/Amount | Adhesion $T_0$ (N/cm) | Adhesion $T_{24}$ (N/cm) | Log Bacteria Reduction | Sterilization (KiloGrays) | Coating Weight (cm) |
|---|---|---|---|---|---|---|---|
| 301 | 20 | GLY/20 | 0.367 | 0.552 | 5.4 | 30 | — |
| 302 | 20 | GLY/25 | 0.293 | 0.448 | 5.4 | 30 | — |
| 303 | 20 | GLY/25 | 0.293 | — | — | 0.000 | — |
| 304 | 20 | PVP/5 GLY/26 | 0.869 | — | — | 0.000 | — |
| 305 | 20 | PVP/10 CBX/27.5 | 1.131 | 1.691 | 5.4 | 0.000 | — |
| 306 | 20 | PVP/10 CBX/27.5 | 0.139 | 0.263 | 5.4 | 0.000 | — |
| 307 | 20 | PVP/10 GLY/27.5 | 0.166 | — | 5.4 | 0.000 | — |
| 308 | 20 | PVP/10 GLY/27.5 | 0.147 | 0.282 | — | 0.000 | — |
| 309 | 20 | PVP/20 GLY/30 | 0.120 | — | — | 0.000 | — |
| 310 | 20 | PVP/20 GLY/48 | 0.147 | — | 5.4 | 0.000 | — |
| 311 | 21 | PVP/10 GLY/27.5 | 0.239 | 0.510 | — | 0.000 | — |
| 312 | 21 | PVP/10 GLY/27.5 | 0.116 | 0.185 | — | 29 | — |
| 313 | 22 | GLY/10 | 0.162 | 0.205 | 5.6 | 0.000 | — |
| 314 | 22 | GLY/20 | 0.212 | 0.247 | 5.6 | 0.000 | — |
| 315 | 23 | GLY/10 | 0.166 | 0.251 | 0.8 | 0.000 | — |
| 316 | 23 | GLY/20 | 0.174 | 0.239 | 1.5 | 0.000 | — |
| 317 | 23 | GLY/20 | 0.185 | 0.263 | 1.2 | 30 | — |
| 318 | 23 | GLY/25 | 0.077 | 0.139 | 3.3 | 30 | — |
| 319 | 23 | GLY/30 | 0.124 | 0.170 | 5.6 | 0.000 | — |
| 320 | 23 | GLY/30 | 0.066 | 0.143 | 0.8 | 30 | — |
| 321 | 24 | GLY/20 | 0.413 | 0.896 | — | 0.000 | — |
| 322 | 24 | GLY/25 | 0.602 | 1.247 | — | 0.000 | — |
| 323 | 24 | GLY/30 | 0.239 | 0.548 | — | 0.000 | — |
| 324 | 25 | GLY/20 | 0.367 | 1.000 | — | 0.000 | — |
| 325 | 25 | GLY/25 | 0.575 | 1.266 | — | 0.000 | — |
| 326 | 25 | GLY/30 | 0.000 | 0.000 | — | 0.000 | — |
| 327 | 26 | GLY/20 | 0.448 | 0.768 | — | 0.000 | — |
| 328 | 26 | GLY/25 | 0.405 | 0.919 | — | 0.000 | — |
| 329 | 26 | GLY/30 | 0.382 | 0.749 | — | 0.000 | — |
| 330 | 27 | PVP/10 GLY/27.5 | 0.475 | 1.096 | — | 0.000 | — |
| 331 | 27 | PVP/10 GLY/27.5 | 0.483 | 1.081 | — | 29 | — |
| 332 | 28 | PVP/10 GLY/27.5 | 0.131 | 0.239 | — | 29 | — |
| 333 | 28 | PVP/10 GLY/27.5 | 0.166 | 0.417 | — | 0.000 | — |
| 334 | 29 | PVP/10 GLY/27.5 | 0.066 | 0.143 | — | 0.000 | — |
| 335 | 29 | PVP/10 GLY/27.5 | 0.108 | 0.317 | — | 29 | — |
| 336 | 30 | PVP/10 GLY/27.5 | 0.208 | 0.475 | — | 29 | — |

TABLE FIVE-continued

Microbial Adhesive Chacteristics
CHLORHEXIDINE GLUCONATE

| Example # | Adhesive # | Transfer Agent Type/Amount | Adhesion $T_0$ (N/cm) | Adhesion $T_{24}$ (N/cm) | Log Bacteria Reduction | Sterilization (KiloGrays) | Coating Weight (cm) |
|---|---|---|---|---|---|---|---|
| 337 | 30 | PVP/10 GLY/27.5 | 0.270 | 0.402 | — | 0.000 | — |
| 338 | 31 | PVP/10 GLY/27.5 | Coagulated | — | — | — | — |
| 339 | 32 | PVP/10 GLY/27.5 | 0.185 | 0.355 | — | 0.000 | — |
| 340 | 32 | PVP/10 GLY/27.5 | 0.255 | 0.502 | — | 29 | — |
| 341 | 32 | PVP/11 GLY/48 | 0.185 | 0.533 | — | 0.000 | — |
| 342 | 33 | PVP/10 GLY/27.5 | 0.513 | 0.930 | — | 29 | — |
| 343 | 33 | PVP/10 GLY/27.5 | 0.251 | 0.000 | — | 0.000 | — |
| 344 | 34 | PVP/10 GLY/27.5 | 0.359 | 0.000 | — | 0.000 | — |
| 345 | 34 | PVP/10 GLY/27.5 | 0.405 | 0.000 | — | 29 | — |
| 346 | 35 | PVP/10 GLY/27.5 | 0.494 | 0.000 | — | 29 | — |
| 347 | 35 | PVP/10 GLY/27.5 | 0.158 | 0.000 | — | 0.000 | — |
| 348 | 36 | PVP/10 GLY/27.5 | 0.205 | 0.290 | — | 29 | — |
| 349 | 36 | PVP/10 GLY/27.5 | 0.251 | 0.023 | — | 0.000 | — |

TABLE SIX

Antimicrobial Adhesive Chacteristics
IODINE

| Example # | Adhesive # | Transfer Agent Type/Amount | Adhesion $T_0$ (N/cm) | Adhesion $T_{24}$ (N/cm) | Log Bacteria Reduction | Sterilization (KiloGrays) | Coating Weight (cm) |
|---|---|---|---|---|---|---|---|
| 350 | 37 | PVP/10 GLY/27.5 | 0.139 | 0.637 | 5.4 | 0 | — |
| 351 | 38 | PVP/10 GLY/27.5 | 0.015 | — | 5.51 | 0.000 | — |
| 352 | 39 | PVP/10 GLY/27.5 | 0.062 | — | 5.51 | 0.000 | — |
| 353 | 40 | PVP/10 GLY/27.5 | 0.073 | — | 5.51 | 0 | — |

LEGEND

| Symbol | Meaning (Units) |
|---|---|
| AA | Acrylic Acid |
| CBX$_{200}$ | Carbowax ™ 200 |
| CBX$_{400}$ | Carbowax ™ 400 |
| EOA | Poly(ethylene oxide) acrylate wherein the number of ethoxy units per acrylate is indicated by the subscripted number provided in conjunction with the wt % (i.e., $5_{16}$ means 5 wt % of a poly(ethylene oxide) acrylate having an average of 16 ethoxy units) EOA$_{16}$ is the acrylate ester of Carbowax ™ 550 purchased from Union Carbide Corp. EOA$_9$ is NK-Ester AM-90G purchased from Shin-Nakamura. |
| GLY | Glycerin |
| IDA | Isodecyl acrylate |
| IOA | Isooctyl acrylate |
| KGray | Sterilizing Gamma Radiation |
| MVTR$_{Up}$ | Moisture Vapor Transmission Rate Measured with Upright Cup (g/cm$^2$/24 hr) |
| MVTR$_{invt}$ | Moisture Vapor Transmission Rate Measured w/ an Inverted Cup (g/cm$^2$/24 hr) |
| NVP | N-vinylpyrrolidone |
| PVP | Poly(N-vinylpyrrolidone) |
| $T_0$ | Skin Adhesion at time (t) = 0 hrs (Newtons/cm width) |
| $T_{24}$ | Skin Adhesion at time (t) = 24 hrs (Newtons/cm width) |

We claim:

1. A low trauma wound dressing having improved moisture vapor permeability comprising layers of (i) a moisture-vapor permeable backing, and (ii) a contiguous particulate adhesive layer of tacky, substantially solvent-insoluble, solvent-dispersible, acrylate-based, elastomeric, pressure-sensitive adhesive microspheres, wherein the adhesive layer further comprises an antimicrobial system effective for achieving a reduction in surface bacteria which includes at least an antimicrobial agent and a transfer agent.

2. The wound dressing of claim 1 wherein the antimicrobial agent is chlorhexidine.

3. The wound dressing of claim 2 wherein the transfer agent is glycerin.

4. The wound dressing of claim 1 wherein the adhesive layer is effective for achieving at least a 2.5 log reduction in surface bacteria.

5. The wound dressing of claim 1 wherein a majority of the adhesive microspheres contain at least one interior void having a diameter of at least about 10% of the diameter of the microsphere.

6. The wound dressing of claim 1 wherein a majority of the adhesive microspheres contain at least one substantially spherical interior void having a diameter of at least about 30% of the diameter of the microsphere.

7. The wound dressing of claim 1 wherein the adhesive microspheres have an average diameter of at least 1 micrometer.

8. The wound dressing of claim 1 wherein the adhesive microspheres are formed from an acrylate polymer having a glass transition temperature of less than about −20° C.

9. The wound dressing of claim 1 wherein the adhesive microspheres are comprised of at least one alkyl acrylate or alkyl methacrylate ester selected from the group consisting of n-butyl acrylate, sec-butyl acrylate, 2-methyl butyl acrylate, 4-methyl-2-penthyl acrylate, 2-ethyl hexyl acrylate, isooctyl acrylate, isononyl acrylate, isoamyl acrylate, isodecyl acrylate, and isodecyl methacrylate.

10. The wound dressing of claim 1 wherein the adhesive microspheres include (a) at least about 75 wt % of at least one alkyl acrylate or alkyl methacrylate ester, and (b) a balance of at least one polar monomer.

11. The wound dressing of claim 10 wherein the alkyl acrylate is selected from the group consisting of (a) an acrylate or methacrylate ester of a non-tertiary $C_{4-12}$ alcohol, and (b) an acrylate or methacrylate ester of a mixture of non-tertiary $C_{1-14}$ alcohols with a resultant average of between about 4–12 carbon atoms per alcohol molecule.

12. The wound dressing of claim 10 wherein the polar monomer is selected from the group consisting of acrylic acid, methacrylic acid, itaconic acid, crotonic acid, maleic acid, fumaric acid, and salts thereof.

13. The wound dressing of claim 1 wherein the adhesive microspheres include (a) at least about 75 wt % of at least one alkyl acrylate or alkyl methacrylate ester, and (b) up to 25 wt % of a combination of (A) a polar monomer selected from the group consisting of acrylic acid, methacrylic acid, itaconic acid, crotonic acid, maleic acid, fumaric acid, and salts thereof, (B) a hydrophilic N-vinyllactam, and (C) a hydrophilic alkylene oxide acrylate having an average of about 3 to 40 alkylene oxide units.

14. The wound dressing of claim 1 wherein the adhesive comprises:

(a) about 70 to 90 wt % microspheres, and (b) about 10 to 30 wt % binder copolymer comprising an elastomeric polymeric backbone having pendant polymeric moieties with the backbone comprised of:

(A) about 50 to 98 wt % of a first monomer comprising an acrylate or methacrylate ester of a non-tertiary $C_{4-12}$ alcohol or an acrylate or methacrylate ester of a mixture of non-tertiary $C_{1-14}$ alcohols with a resultant average of between about 4–12 carbon atoms per alcohol molecule, (B) about 1 to 20 wt % of a second polar monomer copolymerizable with the first monomer, and (C) about 0 to 30 wt % of a third monomer having the general formula X-(Y)$_n$-Z where (1) X is a vinyl group copolymerizable with monomers A and B, (2) Y is a divalent linking group, (3) n is 0 or 1, and (4) Z is a monovalent polymeric moiety having a glass transition temperature of greater than 20° C. with a molecular weight of about 2,000 to about 30,000 and being essentially unreactive under copolymerization conditions.

15. The wound dressing of claim 14 wherein the adhesive microspheres further include at least one polar monomer.

16. The wound dressing of claim 1 wherein the microspheres comprise (a) at least about 85 wt % of an alkyl acrylate ester selected from the group consisting of n-butyl acrylate, sec-butyl acrylate, 2-methyl butyl acrylate, 4-methyl-2-pentyl acrylate, 2-ethyl hexyl acrylate, isooctyl acrylate, isononyl acrylate, isoamyl acrylate, isodecyl acrylate, and isodecyl methacrylate, and (b) up to 15 wt % of at least one polar monomer selected from the group consisting of acrylic acid, methacrylic acid, itaconic acid, crotonic acid, maleic acid, fumaric acid, and salts thereof.

17. The wound dressing of claim 15 wherein the second monomer is selected from the group consisting of acrylic acid, methacrylic acid, itaconic acid, N-vinylpyrrolidone, acrylamide, methacrylamide, acrylonitrile and methacrylonitrile.

18. The wound dressing of claim 15 wherein a majority of the adhesive microspheres contain at least one substantially spherical interior void having a diameter of at least about 10% of the diameter of the microsphere.

19. The wound dressing of claim 8 wherein (a) the adhesive microspheres are formed from non-ionic monomers and comprise a major portion of at least one oleophilic, water-emulsifiable alkyl acrylate or methacrylate ester.

20. The wound dressing of claim 1 wherein (a) the adhesive microspheres consist essentially of:

(A) about 90 to about 99.5 wt % of one or more oleophilic, water-emulsifiable alkyl acrylate esters, at lease one of said esters being selected from the group consisting of isooctyl acrylate, 4-methyl-2-penthyl acrylate, 2-methylbutyl acrylate, sec-butyl acrylate, n-butyl acrylate and 2-ethyl hexyl acrylate, and (B) about 10 to about 0.5 percent by weight of one or more additional monomers selected from the group consisting of a trimethylamine methacrylimide, trimethylamine p-vinylbenzimide, ammonium acrylate, sodium acrylate, N,N-dimethyl-N-(β-methacryloxyethyl) ammonium propionate betaine, 1,1-dimethyl-1-(2,3-dihydroxypropyl) amine methacrylimide, 4,4,9-trimethyl-4-azonia-7-oxo-8-oxa-9-decene-1-sulphonate, 1,1-dimethyl-1-(2,3-dihydroxypropyl) amine methacrylimide, and maleic anhydride; and (b) the adhesive microspheres are prepared by aqueous suspension polymerization in the presence of a suitable emulsifier at a level above said emulsifier's critical micelle concentration.

21. The wound dressing of claim 20 wherein the adhesive microspheres consist essentially of about 98 to about 99.5 wt % alkyl acrylate esters and 0.5 to 2 wt % additional monomers.

22. The wound dressing of claim 1 wherein the backing is polyurethane.

23. The wound dressing of claim 22 wherein the backing is transparent polyurethane having a MVTR$_{up}$ of at least 500 g/m$^2$.

24. A low trauma wound dressing having improved moisture vapor permeability comprising laminated layers of a moisture-vapor permeable backing and a multiple stratum adhesive layer of tacky, substantially solvent-insoluble, solvent-dispersible, acrylate-based, elastomeric, pressure-sensitive adhesive microspheres wherein at least an outermost stratum of the adhesive layers further comprises an antimicrobial system which includes at least an antimicrobial agent and a transfer agent.

25. The wound dressing of claim 24 wherein a majority of the adhesive microspheres contain at least one interior void having a diameter of at least about 10% of the diameter of the microsphere.

26. The wound dressing of claim 24 wherein the adhesive microspheres include (a) at least about 75 wt % of at least one alkyl acrylate or alkyl methacrylate ester, and (b) up to 25 wt % of a combination of (A) a polar monomer selected from the group consisting of acrylic acid, methacrylic acid, itaconic acid, crotonic acid, maleic acid, fumaric acid, and salts thereof, (B) a hydrophilic N-vinyllactam, and (C) a hydrophilic alkylene oxide acrylate having an average of about 3 to 40 alkylene oxide units.

27. The wound dressing of claim 24 wherein the adhesive comprises:
  (a) about 70 to 99 wt % microspheres, and
  (b) about 1 to 30 wt % binder copolymer comprising an elastomeric polymeric backbone having pendant polymeric moieties with the backbone comprised of:
    (A) about 50 to 98 wt % of a first monomer comprising an acrylate or methacrylate ester of a non-tertiary $C_{4-12}$ alcohol or an acrylate or methacrylate ester of a mixture of non-tertiary $C_{1-14}$ alcohols with a resultant average of between about 4–12 carbon atoms per alcohol molecule,
    (B) about 1 to 20 wt % of a second polar monomer copolymerizable with the first monomer, and
    (C) about 1 to 30 wt % of a third monomer having the general formula $X\text{-}(Y)_n\text{-}Z$ where (1) X is a vinyl group copolymerizable with monomers A and B, (2) Y is a divalent linking group, (3) n is 0 or 1, and (4) Z is a monovalent polymeric moiety having a glass transition temperature of greater than 20° C. with a molecular weight of about 2,000 to about 30,000 and being essentially unreactive under copolymerization conditions.

28. The wound dressing of claim 24 wherein (a) the adhesive microspheres are formed from non-ionic monomers and comprise a major portion of at least one oleophilic, water-emulsifiable alkyl acrylate or methacrylate ester, and (b) the adhesive microspheres are prepared by aqueous suspension polymerization in the presence of at least one suitable emulsifier at a concentration level above the emulsifier's critical micelle concentration and a suitable polymeric suspension stabilizer.

29. The wound dressing of claim 24 wherein the backing is polyurethane.

30. A low trauma wound dressing having improved moisture vapor permeability comprising layers of (i) a moisture-vapor permeable backing, and (ii) a particulate adhesive layer containing at least (a) a major amount of a tacky, substantially solvent-insoluble, solvent-dispersible, acrylate-based, elastomeric, pressure-sensitive adhesive microspheres, (b) a minor amount of a binder, and (c) a combination of an antimicrobial agent and a transfer agent effective for achieving a reduction in surface bacteria.

31. The wound dressing of claim 30 wherein the backing is transparent polyurethane having a $MVTR_{up}$ of at least 500 g/m².

32. The wound dressing of claim 30 wherein the adhesive microspheres have an average diameter of at least 1 micrometer.

33. The wound dressing of claim 30 wherein the adhesive microspheres are formed from an acrylate polymer having a glass transition temperature of less than about −20° C.

34. The wound dressing of claim 30 wherein the adhesive microspheres are comprised of at least one alkyl acrylate or alkyl methacrylate ester selected from the group consisting of n-butyl acrylate, sec-butyl acrylate, 2-methyl butyl acrylate, 4-methyl-2-pentyl acrylate, 2-ethyl hexyl acrylate, isooctyl acrylate, isononyl acrylate, isoamyl acrylate, isodecyl acrylate, and isodecyl methacrylate.

35. The wound dressing of claim 30 wherein the adhesive microspheres include (a) at least about 75 wt % of at least one alkyl acrylate or alkyl methacrylate ester, and (b) a balance of at least one polar monomer.

36. The wound dressing of claim 35 wherein the alkyl acrylate is selected from the group consisting of (a) an acrylate or methacrylate ester of a non-tertiary $C_{4-12}$ alcohol, and (b) an acrylate or methacrylate ester of a mixture of non-tertiary $C_{1-14}$ alcohols with a resultant average of between about 4–12 carbon atoms per alcohol molecule.

37. The wound dressing of claim 35 wherein the polar monomer is selected from the group consisting of acrylic acid, methacrylic acid, itaconic acid, crotonic acid, maleic acid, fumaric acid, and salts thereof.

38. The wound dressing of claim 30 wherein the adhesive microspheres include (a) at least about 75 wt % of at least one alkyl acrylate or alkyl methacrylate ester, and (b) up to 25 wt % of a combination of (A) a polar monomer selected from the group consisting of acrylic acid, methacrylic acid, itaconic acid, crotonic acid, maleic acid, fumaric acid, and salts thereof, (B) a hydrophilic N-vinyllactam, and (C) a hydrophilic alkylene oxide acrylate having an average of about 3 to 40 alkylene oxide units.

39. The wound dressing of claim 30 wherein:
  (a) the adhesive microspheres consist essentially of:
    (i) about 90 to about 99.5 wt % of one or more oleophilic, water-emulsifiable alkyl acrylate esters, at least one of said esters being selected from the group consisting of isooctyl acrylate, 4-methyl-2-pentyl acrylate, 2methylbutyl acrylate, sec-butyl acrylate, n-butyl acrylate and 2-ethyl hexyl acrylate, and
    (ii) about 10 to about 0.5 percent by weight of one or more additional monomers selected from the group consisting of trimethylamine methacrylimide, trimethylamine p-vinylbenzimide, ammonium acrylate, sodium acrylate, N,N-dimethyl-N-(β-methacryloxyethyl) ammonium propionate betaine, 1,1-dimethyl-1-(2,3-dihydroxypropyl) amine methacrylimide, 4,4,9-trimethyl-4-azonia-7-oxo-8-oxa-9-decene-1-sulphonate, 1,1 -dimethyl- 1-(2,3-dihydroxypropyl) amine methacrylimide, and maleic anhydride; and
  (b) the adhesive microspheres are prepared by aqueous suspension polymerization in the presence of a suitable emulsifier at a level above said emulsifier's critical micelle concentration.

40. The wound dressing of claim 39 wherein the adhesive microspheres consist essentially of about 98 to about 99.5 wt % alkyl acrylate esters and 0.5 to 2 wt % additional monomers.

41. The wound dressing of claim 30 wherein the adhesive comprises about 10 to 30 wt % binder with the binder comprising a copolymer having an elastomeric polymeric backbone and pendant polymeric moieties with the backbone comprised of (i) about 50 to 98 wt % of a first monomer comprising an acrylate or methacrylate ester of a non-tertiary $C_{4-12}$ alcohol, or an acrylate or methacrylate ester of a mixture of non-tertiary $C_{1-14}$ alcohols with a resultant average of between about 4–12 carbon atoms per alcohol molecule, (ii) about 1 to 20 wt % of a polar second monomer copolymerizable with the first monomer, and (iii) about 0 to 30 wt % of a third monomer having the general formula $X\text{-}(Y)_n\text{-}Z$ where (a) X is a vinyl group copolymerizable with monomers (i) and (ii), (b) Y is a divalent linking group, (c) n is 0 or 1, and (d) Z is a monovalent polymeric moiety having a glass transition temperature of greater than 20° C. with a molecular weight of about 2,000 to about 30,000 and being essentially unreactive under copolymerization conditions.

42. The wound dressing of claim 30 wherein the antimicrobial agent is chlorhexidine.

43. The wound dressing of claim 42 wherein the transfer agent is glycerin.

44. The wound dressing of claim 30 wherein the adhesive layer is effective for achieving at least a 5 log reduction in surface bacteria.

* * * * *